United States Patent [19]

Coy et al.

[11] Patent Number: 5,633,263
[45] Date of Patent: May 27, 1997

[54] LINEAR SOMATOSTATIN ANALOGS

[75] Inventors: David H. Coy, New Orleans; William A. Murphy, Slidell, both of La.

[73] Assignee: The Administrators of the Tulane Educational Fund, New Orleans, La.

[21] Appl. No.: 291,193

[22] Filed: Aug. 15, 1994

Related U.S. Application Data

[63] Continuation-in-part of Ser. No. 839,734, Feb. 19, 1992, abandoned, which is a continuation-in-part of Ser. No. 343,325, Apr. 26, 1989, abandoned.

[51] Int. Cl.$^6$ .................. C07K 14/655; A61K 38/31
[52] U.S. Cl. .................. 530/311; 530/328; 930/160; 930/DIG. 803; 930/DIG. 801; 930/DIG. 800
[58] Field of Search .................. 530/311, 328; 514/16, 2, 806; 930/160, DIG. 803, DIG. 801, DIG. 800

[56] References Cited

U.S. PATENT DOCUMENTS

| | | | |
|---|---|---|---|
| 4,020,157 | 4/1977 | Abraham et al. | 530/311 |
| 4,238,481 | 12/1980 | Rink et al. | 530/311 |
| 4,358,439 | 11/1982 | Sieber et al. | 530/311 |
| 4,369,179 | 1/1983 | Rink et al. | 424/177 |
| 4,485,101 | 11/1984 | Coy et al. | 424/177 |
| 4,853,371 | 8/1989 | Coy et al. | 530/311 |

FOREIGN PATENT DOCUMENTS

| | | |
|---|---|---|
| 0 030 920 | 12/1980 | European Pat. Off. . |
| 0 187 622 | 8/1990 | European Pat. Off. . |
| 2 206 352 | 1/1989 | United Kingdom . |

OTHER PUBLICATIONS

Kazmierski et al., Tetrahedron 44:697–710, 1988.
Manning, M., et al. (1987) Nature 329, 539–540.
Manning, et al., (1988) Int. J. Peptide Protein Res. 32:455–467.
Kazmierski et al. (1988) J. Med. Chem. 31:2170–2177.
Rivier et al, Journal of Medicinal Chemistry, vol. 18(2), pp. 123–126, (Feb./1975).
Strachan et al, Chem. Abs., vol. 91(25), 211830, (1979).
Cai et al., Peptides, Sep. 11, 1987, pp. 627–629.
Hoefer et al., 1984, Mol. Cell. Endocrinol. 35:229.
Ben–Jonathan et al., 1983, Methods Enzymol. 103;249.
Heiman et al., 1985, Endocrinology 116:410.
European Search Report.
PCT International Search Report.
Vecsei et al, CA 99(23), 1881539 (1983).
Freidinger et al, In Peptides, Proceedings of the 8th Am. Pept. Symposium, (1983), pp. 349–352.
Weber et al, Surgery, vol. 102(6), pp. 974–987, (Dec. 1987).

*Primary Examiner*—Ponnathapura Achutamurthy
*Assistant Examiner*—T. D. Wessendorf
*Attorney, Agent, or Firm*—Fish & Richardson P.C.; William E. McGowan

[57] ABSTRACT

Linear peptide analogs of somatostatin having the formula:

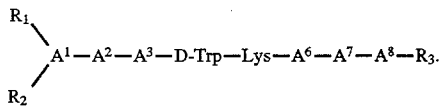

As an example, D-Phe-Phe-Phe-D-Trp-Lys-Thr-Phe-Thr is covered by the above formula (i.e., $R_1$ is H, $R_2$ is H, $A^1$ is D-Phe, $A^2$ is Phe, $A^3$ is Phe, $A^6$ is Thr, $A^7$ is Phe, $A^8$ is Thr, and $R_3$ is $NH_2$).

16 Claims, 2 Drawing Sheets

LINEAR SOMATOSTATIN ANALOGS

This is a continuation-in-part of application Ser. No. 07/839,734, filed Feb. 19, 1992, now abandoned, which in turn, is a continuation-in-part of application Ser. No. 07/343,325, filed Apr. 26, 1989, now abandoned.

This invention was made in the course of work under a grant or award from the U.S. government; therefore, the U.S. government has rights in the invention.

BACKGROUND OF THE INVENTION

This invention relates to therapeutic peptides.

A number of somatostatin analogs exhibiting Growth Hormone-releasing-inhibiting activity have been described in the literature, including analogs containing fewer than the naturally occurring fourteen amino acids. For example, Coy et al. U.S. Pat. No. 4,485,101, hereby incorporated by reference, describes dodecapeptides having an N-terminal acetyl group, a C-terminal $NH_2$, D-Trp at position 6, and p-Cl-Phe at position 4. (Herein, when no designation of configuration is given, the L-isomer is intended.)

Abbreviations: Nle=norleucine, Nal—naphthylalanine

SUMMARY OF THE INVENTION

In general, the invention features a linear somatostatin analog of the formula:

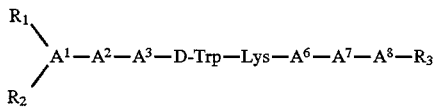

wherein $A^1$ is a D- or L-isomer of any of Ala, pyridyl-Ala, Leu, Ile, Val, Met, Nle, Thr, Ser, Trp, β-Nal Phe, o-X-Phe (wherein X=$CH_3$, Cl, Br, F, OH, $OCH_3$, $NO_2$), p-X-Phe (wherein X=$CH_3$, Cl, Br, F, OH, $OCH_3$, $NO_2$), 2,4-dichloro-Phe, pentafluoro-Phe;

$A^2$ is any of Ala, pyridyl-Ala, Leu, Ile, Val, Met, Nle, Trp, β-Nal Phe, o-X-Phe (wherein X=$CH_3$, Cl, Br, F, OH, $OCH_3$, $NO_2$), p-X-Phe (wherein X=$CH_3$, Cl, Br, F, OH, $OCH_3$, $NO_2$), 2,4-dichloro-Phe, or pentafluoro-Phe;

$A^3$ is any of Ala, pyridyl-Ala, Leu, Ile, Val, Met, Nle, Trp, Tyr, β-Nal Phe, o-X-Phe (wherein X=$CH_3$, Cl, Br, F, OH, $OCH_3$, $NO_2$), p-X-Phe (wherein X=$CH_3$, Cl, Br, F, OH, $OCH_3$, $NO_2$), 2,4-dichloro-Phe, or pentafluoro-Phe;

$A^6$ is any of Ala, pyridyl-Ala, Leu, Ile, Val, Lys, Met, Nle, Thr, Ser, Trp, β-Nal, o-X-Phe (wherein X=$CH_3$, Cl, Br, F, OH, $OCH_3$, $NO_2$), p-X-Phe (wherein X=$CH_3$, Cl, Br, F, OH, $OCH_3$, $NO_2$), 2,4-dichloro-Phe, or pentafluoro-Phe;

$A^7$ is any of Ala, pyridyl-Ala, Leu, Ile, Val, Met, Nle, Trp, β-Nal Phe, o-X-Phe (wherein X=$CH_3$, Cl, OH, $OCH_3$, $NO_2$), p-X-Phe (wherein X=$CH_3$, Cl, Br, F, OH, $OCH_3$, $NO_2$), 2,4-dichloro-Phe, or pentafluoro-Phe;

$A^8$ is a D- or L-isomer of any of Ala, pyridyl-Ala, Leu, Ile, Ser, Thr, Val, Met, Nle, Trp, β-Nal Phe, o-X-Phe (wherein X=$CH_3$, Cl, Br, F, OH, $OCH_3$, $NO_2$), p-X-Phe (wherein X=$CH_3$, Cl, Br, F, OH, $OCH_3$, $NO_2$), 2,4-dichloro-Phe, or pentafluoro-Phe;

each $R_1$ and $R_2$, independently, is H, lower (1–5 carbon atoms) acyl, or lower alkyl; and $R_3$ is OH, $NH_2$, or lower alkyl; provided that at least one of $A^1$ and $A^2$ and at least one of $A^7$ and $A^8$ aromatic amino acid; and further provided that $A^1$, $A^2$, $A^7$ and $A^8$ cannot all be aromatic amino acids or a pharmaceutically acceptable salt thereof.

In the formula recited above and in the claims, $A^1$ stands for an amino acid residue of =N—CH(R)—C=O— and each of $A^2$ through $A^8$ stands for —NH—CH(R)—C=O—, where R is the identifying group of an amino acid, e.g., R is —$CH_3$ for Ala.

Preferably, of $A^1$ and $A^2$, only one is an aromatic amino acid; and of $A^7$ and $A^8$, only one is an aromatic amino acid.

In preferred embodiments $A^1$ is a D-isomer of any of Trp, β-Nal, o-X-Phe (wherein X=$CH_3$ or $OCH_3$), p-X-Phe (wherein X=$CH_3$ or $OCH_3$) and $A^8$ is a D- or L-isomer of any of Ala, pyridyl-Ala, Leu, Ile, Ser, Thr, Val, Met, Nle, o-X-Phe (wherein X=Cl, Br, F, OH, $NO_2$), p-X-Phe (wherein X=Cl, Br, F, OH, $NO_2$), 2,4-dichloro-Phe, or pentafluoro-Phe.

In other preferred embodiments $A^1$ is a D-isomer of any of o-X-Phe (wherein X=H, Cl, Br, F, OH, or $NO_2$), p-X-Phe (wherein X=H, Cl, Br, F, OH, or $NO_2$), 2,4-dichloro-Phe, or pentafluoro-Phe; and $A^8$ is a D- or L-isomer of any of Ala, pyridyl-Ala, Leu, Ile, Thr, Val, Met, Nle, Trp, β-Nal, o-X-Phe (wherein X=$CH_3$ or $OCH_3$), or p-X-Phe (wherein X=$CH_3$ or $OCH_3$).

In other preferred embodiments $A^8$ is a D- or L-isomer of any of Thr, Trp, β-Nal, o-X-Phe (wherein X=$CH_3$ or $OCH_3$), or p-X-Phe (wherein X=$CH_3$ or $OCH_3$); and $A_1$ is Phe or a D-isomer of any of Ala, pyridyl-Ala, Leu, Ile, Val, Met, Nle, o-X-Phe (wherein X=H, Cl, Br, F, OH, $NO_2$), p-X-Phe (wherein x=H, Cl, Br, F, OH, $NO_2$), 2,4-dichloro-Phe, or pentafluoro-Phe.

In other preferred embodiments $A^8$ is a D- or L-isomer of any of Ser, Thr, o-X-Phe (wherein X=Cl, Br, F, OH, or $NO_2$), p-X-Phe (wherein X=Cl, Br, F, OH, or $NO_2$), 2,4-dichloro-Phe, or pentafluoro-Phe; and $A^1$ is a D-isomer of any of Ala, pyridyl-Ala, Leu, Ile, Val, Met, Nle, Trp, β-Nal, o-X-Phe (wherein X=$CH_3$ or $OCH_3$), or p-X-Phe (wherein X=$CH_3$ or $OCH_3$).

More preferably, $A^1$=β-D-Nal or D-Phe; $A^2$=Ala, Phe or p-chloro-Phe; $A^3$=Tyr or Phe; $A^6$=Val, Lys or Thr; $A^7$=Ala or Phe; $A^8$=Thr or D-β-Nal. While a D-isomer is preferred as the C-terminal residue (which is well known in the art to confer stability on the peptides), analogs with an L-isomer at that position are also within the invention. Similarly, the N-terminal residue can either be of D-or L-configuration.

Preferred compounds of the invention include D-phe-p-chloro-phe-Tyr-D-Trp-Lys-Thr-phe-Thr-$NH_2$; D-Phe-p-$NO_2$-Phe-Tyr-D-Trp-Lys-Val-Phe-Thr-$NH_2$; D-Nal-p-chloro-Phe-Tyr-D-Trp-Lys-Val-Phe-Thr-$NH_2$; D-Phe-p-chloro-Phe-Tyr-D-Trp-Lys-Val-Phe-Thr-$NH_2$; D-Phe-Phe-Tyr-D-Trp-Lys-Val-Phe-Thr-$NH_2$; D-Phe-Phe-Phe-D-Trp-Lys-Thr-Phe-Thr-$NH_2$; and D-Phe-Ala-Tyr-D-Trp-Lys-Val-Ala-B-D-Nal-$NH_2$.

In other preferred embodiments, a therapeutically effective amount of the therapeutic compound and a pharmaceutically acceptable carrier substance, e.g. magnesium carbonate, lactose, or a phospholipid with which the therapeutic compound can form a micelle, together form a therapeutic composition, e.g. a pill, tablet, capsule, or liquid for oral administration to a human patient, a spreadable cream, gel, lotion, or ointment to be applied topically or to be iontorphoretially forced through the skin of a human patient in need of the compound, a liquid capable of being administered nasally as drops or spray, or a liquid capable of intravenous, parenteral, subcutaneous, or intraperitoneal administration. The pill, tablet or capsule can be coated with a substance capable of protecting the composition from the gastric acid in the patient's stomach for a period of time sufficient to allow the composition to pass undisintegrated into the patient's small intestine. The therapeutic composition can also be in the form of a biodegradable or nonbiodegradable sustained release formulation for intramuscular administration. For maximum efficacy, zero order release is desired, and can be obtained using an implantable or external pump, e.g., INFUSOID™ pump, to administer the therapeutic composition.

The compounds of the invention are active in inhibiting the secretion of growth hormone, somatomedins (e.g., IGF-1), insulin, glucagon, and other autoparacrine growth factors or pancreatic growth factors. The compounds of the invention are acyclic and, therefore, stable and resistant to oxidation. In addition, the acyclic nature of the peptide facilitates synthesis and purification, improving efficiency and reducing manufacturing costs.

Other features and advantages of the invention will be apparent from the following description of the preferred embodiments thereof, and from the claims.

DESCRIPTION OF THE PREFERRED EMBODIMENTS

The drawings will first be described.

Drawings

Structure

Figure 1:
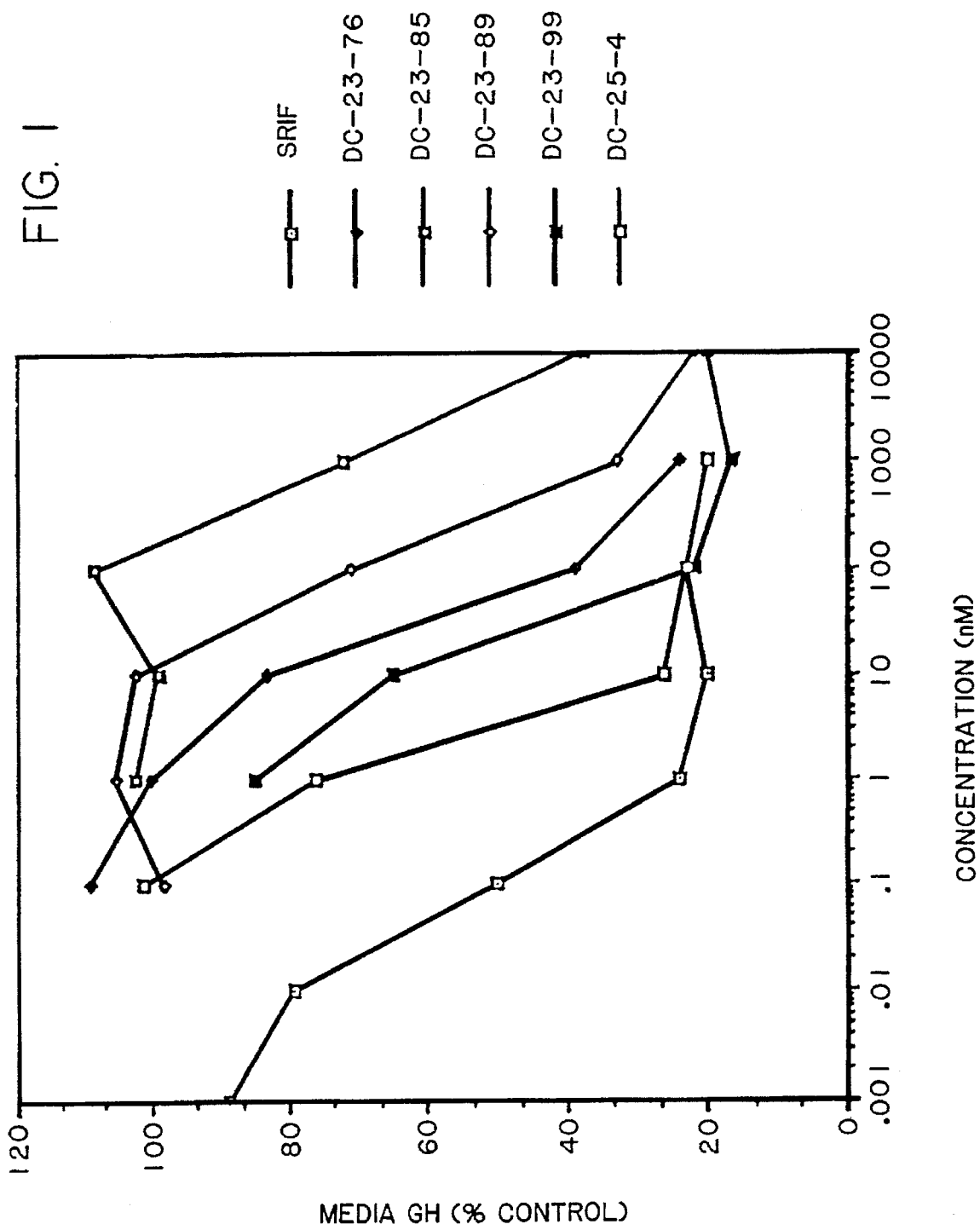
FIG. 1 is a graph showing the effects of linear analogs on growth hormone secretion by rat pituitary cells.

The compounds of the invention have the general formula recited in the Summary of the Invention, above. They are all octapeptide analogs of somatostatin which have D-Trp at the fourth position and Lys at the fifth position. An octapeptide of this invention contains at least an aromatic amino acid at position $A^1$ or $A^8$ and at least an aromatic amino acid at position $A^2$ or $A^7$, but cannot contain an aromatic amino acid at each of $A^1$, $A^2$, $A^7$ and $A^8$. In other words, while at least one aromatic acid must be present at either terminus, $A^1$, $A^2$, $A^7$ and $A^8$ cannot all be aromatic amino acids.

The compounds can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

The synthesis of one therapeutic peptide follows. Other peptides can be prepared by making appropriate modifications, within the ability of someone of ordinary skill in this field, of the following synthetic method.

The first step in the preparation of the peptide

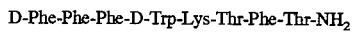
D-Phe-Phe-Phe-D-Trp-Lys-Thr-Phe-Thr-NH$_2$ is the preparation of the intermediate:
Boc-D-Phe-Phe-Phe-D-Trp-N-benzyloxycarbonyl-Lys-O-benzyl-Thr-Phe-O-benzyl-Thr-benzhydrylamine resin, as follows.

Benzhydrylamine-polystyrene resin (Advanced ChemTech, Inc.) (1.2 g, 0.5 mmole) in the chloride ion form is placed in the reaction vessel of an Advanced ChemTech peptide synthesizer programmed to perform the following reaction cycle:

(a) methylene chloride;
(b) 33% trifluoroacetic acid in methylene chloride (2 times for 1 and 25 min each);
(c) methylene chloride;
(d) ethanol;
(e) methylene chloride; and
(f) 10% triethylamine in chloroform.

The neutralized resin was stirred with Boc-O-benzyl-threonine and diisopropylcarbodiimide (1.5 mmole each) in methylene chloride for 1 hr and the resulting amino acid resin is then cycled through steps (a) to (f) in the above wash program. The following amino acids (1.5 mmole) are then coupled successively by the same procedure:

Boc-Phe, Boc-O-benzyl-Thr, Boc-N-benzyloxycarbonyl-lysine, Boc-D-Trp, Boc-Phe, and Boc-Phe and Boc-D-Phe. After washing and drying, the completed resin weighed 1.70 g.

The resin (1.70 g, 0.5 mmole) is then mixed with cresol (5 ml), dithiothreitol (100 mg) and anhydrous hydrogen fluoride (35 ml) at 0° C. and stirred for 45 min. Excess hydrogen fluoride is evaporated rapidly under a stream of dry nitrogen, and free peptide precipitated and washed with ether. The crude peptide is then dissolved in a minimum volume of 50% acetic acid and eluted on a column (2.5×100 cm) of SEPHADEX G-25 using the same solvent. Fractions containing a major component by UV absorption and thin layer chromatography are then pooled, evaporated to a small volume and applied to a column (2.5×50 cm) of VYDAC octadecylsilane silica (10–15 μM).

The column was eluted with a linear gradient of 10–45% acetonitrile in 0.1% trifluoroacetic acid in water. Fractions are examined by thin layer chromatography and analytical high performance liquid chromatography and pooled to give maximum purity. Repeated lyophilization of the solution from water gives 65 mg of the product as a white, fluffy powder.

The product was found to be homogeneous by hplc and tlc. Amino acid analysis of an acid hydrolysate confirms the composition of the octapeptide.

Other peptides of the invention are prepared in an analogous fashion to those described above.

Effects of Linear Somatostatin Analogs on Growth Hormone Secretion in Cultured Rat Pituitary Cell Dispersion Octapeptides of the invention are tested for inhibtion of growth hormone-releasing-activity using rat pituitary cells, as follows.

Anterior pituitaries from adult Charles River CD male rats (Wilmington, Mass.) weighing 200–250 g and housed under controlled conditions (lights on from 0500–1900 h), were dispersed and cultured using aseptic technique by modification of previously described methods (Hoefer et al., 1984, Mol. Cell. Endocrinol. 35:229; Ben-Jonathan et al., 1983, Methods Enzymol. 103:249; Heiman et al., 1985, Endocrinology 116:410). Pituitaries were removed from decapitated rats, sectioned, and then placed into a siliconized, liquid scintillation vial containing 2 ml 0.2% trypsin (Worthington Biochemicals, Freehold, N.J.) in sterile-filtered Krebs-Ringer bicarbonate buffer supplemented with 1% bovine serum albumin, 14 mM glucose, modified Eagle medium (MEM) vitamin solution and MEM amino acids (Gibco Laboratories, Grand Island, N.Y.) (KRBGA). All glassware was siliconized as described by Sayers et al., 1971, Endocrinology 88:1063. The fragments were incubated in a water bath for 35 min at 37° C. with agitation. The vial contents then were poured into a scintillation vial containing 2 ml 0.1% DNase (Sigma Chemical Co., St. Louis, Mo.) in KRBGA and incubated for 2 min at 37° C. with agitation. After incubation the tissue was decanted back into the centrifuge tube and allowed to settle. Medium was discarded, and pituitary sections were washed 3 times with 1 ml fresh KRBGA. The cells were then dispersed by gently drawing the fragments into and expelling them out of a siliconized, fire-polished Pasteur pipette in 2 ml 0.05% LBI (lima beam trypsin inhibitor, Worthington Biochemicals). Dispersed cells were filtered through a 630 μm diameter Nylon mesh (Tetko, Elmsford, N.Y.) into a fresh 15 ml centrifuge tube and harvested by centrifugation at 100×g for 1 min. The final speed was attained gradually through a centrifugation period of 17 min.

After centrifugation, medium was discarded and the pelleted cells were resuspended in fresh LBI (2 ml) with a Pasteur pipette. The dispersed cells were then diluted with approximately 15 ml sterile-filtered Dulbecco's modified Eagle medium (GIBCO), which was supplemented with 2.5% fetal calf serum (GIBCO), 3% horse serum (GIBCO), 10% fresh rat serum (stored on ice for no longer than 1 h) from the pituitary donors, 1% MEM nonessential amino acids (GIBCO), gentamycin (10 ng/ml; Sigma) and nyatatin (10,000 U/ml; GIBCO). The cells were poured into a 50 ml round-bottomed glass extraction flask with a large diameter opening and were counted with a lemacytometer (approximately 2,000,000 cells per pituitary) and randomly plated at a density of 200,000 cells per well (Co-star cluster 24; Rochester Scientific Co., Rochester, N.Y.). The plated cells were maintained in the above Dulbecco's medium in a humidified atmosphere of 95% air and 5% $CO_2$ at 37° C. for 96 h.

In preparation for a hormone challenge, the cells were washed 3× with medium 199 (GIBCO) to remove old medium and U floating cells. Each dose of analog (diluted in normal saline in siliconized test tubes) was tested in the presence of 1 nM GRF(1–29)$NH_2$ (growth hormone releasing factor) in quadruplicate wells in a total volume of 1 ml medium 199 containing 1% BSA (fraction V; Sigma). After 3 h. at 37° C. in an air/carbon dioxide atmosphere (95/5%), the medium was removed and stored at –20° C. until assayed for hormone content. Growth hormone was measured in a conventional radioimmunoassay using anti-growth hormone antibody.

Figure 2:
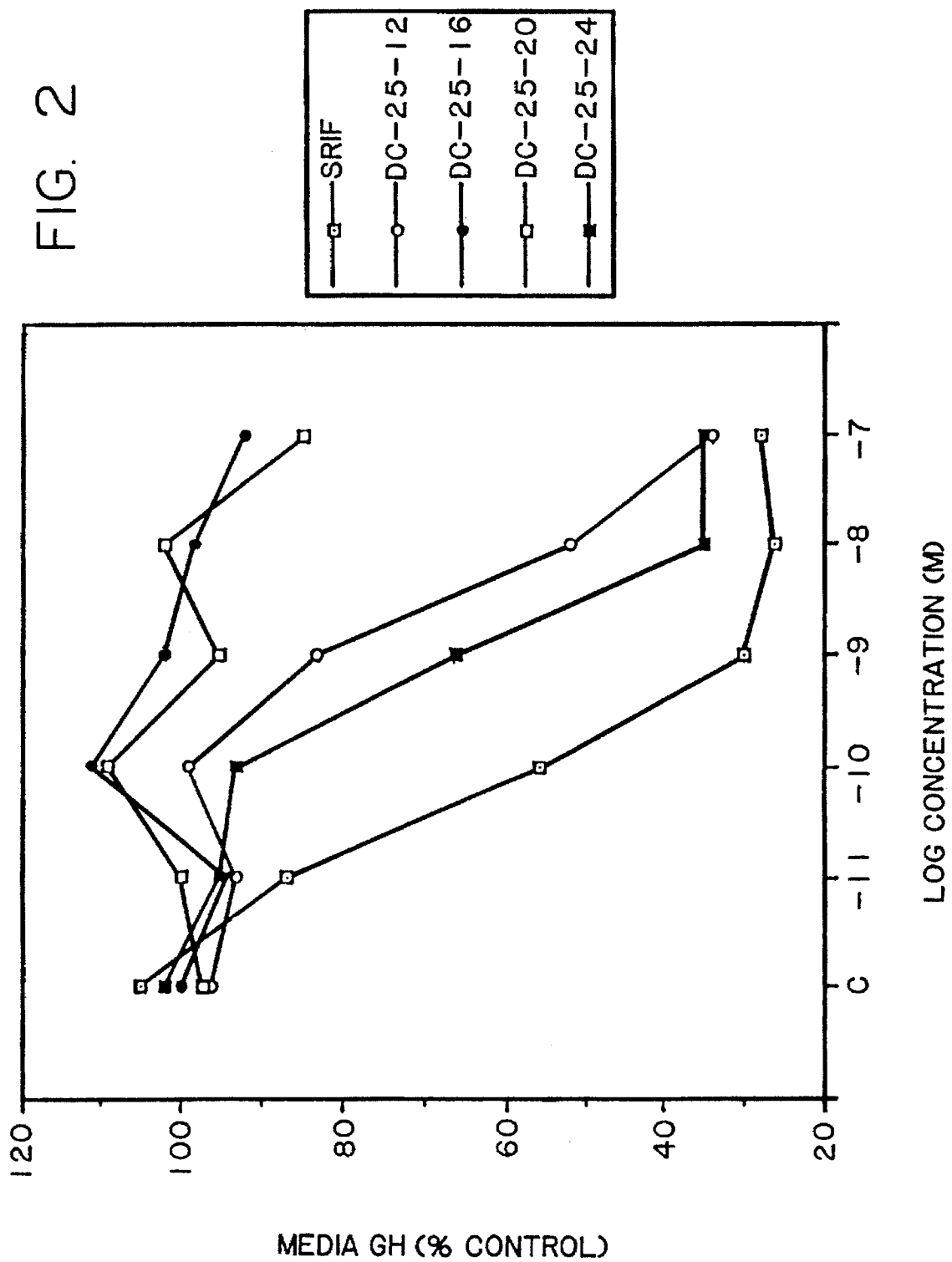
FIG. 2 is a graph showing the effects of linear analogs on growth hormone secretion by rat pituitary cells.

The effect of 9 different peptides on the release of growth hormone in cultured rat pituitary cells is shown in FIGS. 1 and 2. The peptides DC-25-4 (FIG. 1) and DC-25-24 (FIG. 2) are most active in inhibiting the release of growth hormone. Both DC-25-4 and DC-25-24 contain an electron withdrawing group near one end of the molecule and an electron donating group near the opposite end of the molecule. Peptides DC-23-85 (FIG. 1) and DC-25-16 (FIG. 2), which are not within the present invention, show essentially no activity.

Inhibition of $I^{125}$ Somatotropin-release-inhibiting Factor (SRIF-14) Binding by Linear Somatostatin Analogs Crude membrane preparations were obtained from rat pancreas, cerebral cortex, or human small cell lung carcinoma (NCI-H69) cells by homogenizing (Polytron, setting 6, 15 sec) the tissues or cells in ice-cold 50 mM Tris-HCl and centrifuging twice at 39,000× g (10 min), with an intermediate resuspension in fresh buffer. The final pellets were resuspended in 10 mM Tris-HCl for assay. Aliquots of the membrane preparation were incubated for 25 min at 30° C. with labeled somatotropin-release-inhibiting factor, [$^{125}$I-Tyr$^{11}$] SRIF-14 (2000 Ci/mmol, Amersham Corp.), in 50 mM HEPES (pH 7.4) containing bovine serum albumin (10 mg/ml; fraction V, Sigma Chem.), $MgCl_2$ (5mM), Trasylol (200 KIU/ml), bacitracin (0.02 mg/ml), and phenylmethylsulphonyl fluoride (0.02 mg/ml). The final assay volume was 0.3 ml. The incubations were terminated by rapid filtration through Whatman GF/C filters (pre-soaked in 0.3% polyethylenimine) under reduced pressure. Each tube and filter were then washed three times with 5 ml aliquots of ice-cold buffer. Specific binding was defined as the total [$^{125}$I]SRIF-14 bound minus that bound in the presence of 200 nM unlabelled SRIF-14.

Table 1 gives results of inhibition of [$^{125}$I]SRIF-14 binding by linear peptides of the invention. The concentration of [$^{125}$I]SRIF-14 was approximately 0.05 nM. (Values in parenthesis indicate the number of independent determinations.) The $IC_{50}$ (concentration of analog resulting is 50% competitive inhibition) in nM values are indicated for pancreas, small cell lung carcinoma (SCLC), and brain. The results show that analogs DC-25-4 and DC-23-99 are particularly effective in inhibiting the binding of $I^{125}$ SRIF-14. Peptide DC-23-85, which is not within the invention, inhibits the binding of $I^{125}$SRIF-14 only poorly.

Use

When administered to mammals, particularly humans, (e.g. orally, topically, intravenously, parenterally in a sustained release, biodegradable or nonbiodegradable form, nasally, or by suppository), the compounds can be effective to inhibit growth hormone release as well as to inhibit somatomedins (e.g., IGF-1), insulin, glucagon, other auto-paracrine growth factors or pancreatic exocrine secretion, and to therapeutically affect the central nervous system.

The compounds can be administered to a mammal, e.g. a human, in the dosages used for somatostatin or, because of their greater potency, in smaller dosages. The compounds of the invention can be used for the treatment of cancer, particularly growth hormone-dependent cancer (e.g., bone, cartilage, pancreas (endocrine and exocrine), prostate, or breast), acromegaly and related hypersecretory endocrine states, or of bleeding ulcers in emergency patients and in those suffering from pancreatitis or diarrhea. The compounds can also be used in the management of diabetes and to protect the liver of patients suffering from cirrhosis and hepatitis. The compounds can also be used to treat Alzheimer's disease, as analgesics to treat pain by acting specifically on certain opiate receptors, and as gastric cytoprotective compounds for ulcer therapy. The compounds can also be used to treat certain types of mushroom poisoning.

The compounds can also be used to treat diabetes-related retinopathy. The anti-cancer activity of the compounds may be related to their ability to antagonize cancer-related growth factors such as epidermal growth factor.

The compounds can be administered to a mammal, e.g., a human, in a dosage of 0.01 to 1000 mcg/kg/day, preferably 0.1 to 100 mcg/kg/day.

Mechanism

The activity of previously described analogs of somatostatin is dependent on the presense of a disulfide linkage between cysteine residues located at or near the ends of the peptide, see, e.g., Coy et al. U.S. Pat. No. 4,485,101, hereby incorporated by reference. The disulfide linkage results in a cyclic conformation necessary for activity.

The inclusion of a disulfide linkage is an undesirable feature in these synthetic peptides in that the step favoring synthesis of the disulfide linkage imposes a dramatic decrease in the overall yield of the synthesis. Furthermore, the disulfide linkages are subject to oxidation and thus result in a less stable product.

The instant invention avoids the use of disulfide linkages and their attendant drawbacks. The octapeptides of the instant invention utilize non-covalent interactions between the side chains of critically positioned constituent amino acid residues to confer a hairpin or quasi-cyclic conformation on the peptides.

The side chains and substituted side chains of the amino acid residues of the instant invention are subject to two types of interactions that tend to confer the desired tertiary structure on the peptide. The first type of interaction occurs when amino acids bearing hydrophobic side chains are located at or near both ends of the peptide. Peptides of this structure exploit the tendency of hydrophobic moieties to avoid contact with polar substances. Interactions between the hydrophobic groups at each end of the peptide, favored over interactions between these groups and the polar solvents of physiological environments, confer a hairpin or quasi-cyclic configuration on the peptide.

The second type of interaction arises as a result of the interaction of electron-donating and electron-withdrawing moieties of amino acids at opposite ends of the peptide. The invention features peptides in which an amino acid possessing an electron-donating group resides in one end region of the peptide while an amino acid possessing an electron-withdrawing group resides in the other end region of the peptide. The attraction between the electron-donating group, at one end of the peptide, and the electron-withdrawing group, at the other end of the peptide, acts to confer a hairpin or quasi-cyclic structure on the peptide. Both hydrophobic-hydrophobic interactions and electron donor-elctron withdrawer interactions may be active in a given peptide.

Other embodiments are within the following claims.

TABLE I

TABLE 1
Inhibition of $I^{125}$ SRIF-14 binding by linear analogs of somatostatin
$IC_{50}$ (nM)

| Analog | Pancreas | SCLC | Brain |
|---|---|---|---|
| Somatostatin | 0.53 (5) | 4.2 (5) | 0.53 (3) |
| BIM-23053/DC-25-4 | 2.8 (2) | 2.2 (1) | 109 |
| BIM-23052/DC-23-99 | 9.4 (1) | 1.2 (1) | 7.3 (1) |
| BIM-23049/DC-23-76 | 9.2 (3) | 2.1 (1) | >10,000 (1) |
| BIM-23051/DC-23-89 | 34 (2) | 15 (1) | >10,000 (1) |
| BIM-23050/DC-23-85 | 264 (1) | — | 2,189 (2) |

Results are expressed as the concentration in nM of analog that gives 50% inhibition of $I^{125}$ SRIF-14 binding ($IC_{50}$). The numbers in parantheses indicate the number of trials. The structure of the analogs is as follows: BIM-23049/DC-23-76—β-D-Nal-Ala-Tyr-D-Trp-Lys-Val-Ala-Thr-$NH_2$; BIM-23050/DC-23-85-n-methyl-D-Ala-Tyr-D-Trp-Lys-Val-Phe-$NH_2$; BIM-23051/DC-23-89-D-Phe-Ala-Phe-D-Trp-Lys-Thr-Ala-Thr-$NH_2$; BIM-23052/DC-23-99-D-Phe-Phe-Phe-D-Trp-Lys-Thr-Phe-Thr-$NH_2$; BIM-23053/DC-25-4-D-Phe-Ala-Tyr-D-Trp-Lys-Val-Ala-β-D-Nal-$NH_2$. The structure of SRIF-14 is: Ala-Gly-Cys-Lys-Asn-Phe-Phe-Trp-Lys-Thr-Phe-Ser-OH.

What is claimed is:

1. An octapeptide of the formula:

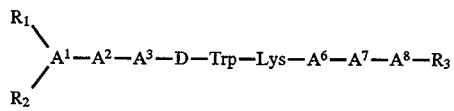

wherein $A^1$ is a D-isomer of β-Nal, Phe, 2,4-dichloro-Phe, pentafluoro-Phe, p-X-Phe, or o-X-Phe, wherein X is $CH_3$, Cl, Br, F, OH, $OCH_3$, or $NO_2$;

$A^2$ is Ala, Phe, β-Nal, 2,4-dichloro-Phe, pentafluoro-Phe, o-X-Phe, or p-X-Phe, wherein X is $CH_3$, Cl, Br, F, OH, $OCH_3$, or $NO_2$;

$A^3$ is Phe, β-Nal, Trp, 2,4-dichloro-Phe, pentafluoro-Phe, o-X-Phe, or p-X-Phe, wherein X is $CH_3$, Cl, Br, F, OH, $OCH_3$, or $NO_2$;

$A^6$ is Val, Ala, Leu, Ile, Nle, Thr, or Ser;

$A^7$ is Ala, Phe, β-Nal, 2,4-dichloro-Phe, Pentafluoro-Phe, o-X-Phe, or p-X-Phe, wherein X is $CH_3$, Cl, Br, F, OH, $OCH_3$, or $NO_2$;

$A^8$ is a D- or L-isomer of Thr, Ser, Phe, β-Nal, [pyridyl-Ala, Trp,]2,4-dichloro-Phe, pentafluoro-Phe, p-X-Phe, or o-X-Phe, wherein X is $CH_3$, Cl, Br, F, OH, $OCH_3$, or $NO_2$;

each $R_1$ and $R^2$, independently, is H, $C_{1-5}$ acyl or $C_{1-5}$ alkyl; and $R_3$ is OH or $NH_2$; provided that at least one of $A^1$ and $A^2$ and one of $A^7$ and $A^8$ must be one of the aromatic amino acid assigned thereto; and further provided that each of $A^1$, $A^2$, $A^7$, and $A^8$ cannot all be one of the aromatic amino acids assigned thereto; or a pharmaceutically acceptable salt thereof.

2. An octapeptide of claim 1, wherein $A^1$ is a D-isomer of β-Nal, Phe, or p-X-Phe, where X is $CH_3$, Cl, Br, F, CH, $OCH_3$, or $NO_2$;

$A^2$ is Ala, Phe, β-Nal, or p-X-Phe, where X is $CH_3$, Cl, Br, F, OH, $CH_3$, or $NO_2$;

$A^3$ is Trp, Phe, β-Nal, or p-X-Phe, where X is $CH_3$, Cl, Br, F, OH, $OCH_3$, or $NO_2$;

$A^6$ is Val, Thr, or Ser;

$A^7$ is Ala, Phe, β-Nal, or p-X-Phe, where X is $CH_3$, Cl, Br, F, OH, $OCH_3$, or $NO_2$; and $A^8$ is the D- or L-isomer of Thr, Phe, β-Nal, or p-X-Phe, where X is $CH_3$, Cl, Br, F, OH, $OCH_3$, or $NO_2$.

3. An octapeptide of claim 2, wherein $A^2$ is Phe, β-Nal, or p-X-Phe, where X is $CH_3$, Cl, Br, F, OH, $OCH_3$, or $NO_2$;

$A^7$ is Phe; and $A^8$ is Thr.

4. An octapeptide of claim 2, wherein $A^2$ is Ala.

5. An octapeptide of claim 4, wherein $A^7$ is Ala; and $A^8$ is the D- or L-isomer of Phe, β-Nal, or p-X-Phe, where X is $CH_3$, Cl, Br, F, OH, $OCH_3$, or $NO_2$.

6. An octapeptide of claim 2, wherein $A^1$ is D-Phe, D-p-Cl-Phe, D-β-Nal, or D-Tyr;

$A^2$ is Ala, Phe, p-Cl -Phe, or p-$NO_2$-Phe;

$A^3$ is Phe, Tyr, or Trp;

$A^7$ is Ala or Phe; and $A^8$ is Thr, β-Nal, or β-D-Nal.

7. An octapeptide of claim 6, wherein
$A^2$ is Phe, p-Cl-Phe, or p-NO$_2$-Phe;
$A^7$ is Phe; and
$A^8$ is Thr.

8. An octapeptide of claim 6, wherein $A^2$ is Ala.

9. An octapeptide of claim 6, wherein
$A^7$ is Ala; and
$A^8$ is β-Nal or β-D-Nal.

10. An octapeptide of claim 7 of the formula:

D-Phe-p-Cl-Phe-Tyr-D-Trp-Lys-Thr-Phe-Thr-NH$_2$.

11. An octapeptide of claim 7 of the formula:

D-Phe-p-NO2-Phe-Tyr-D-Trp-Lys-Val-Phe-Thr-NH$_2$.

12. An octapeptide of claim 7 of the formula:

D-Nal-p-Cl-Phe-Tyr-D-Trp-Lys-Val-Phe-Thr-NH$_2$.

13. An octapeptide of claim 7 of the formula:

D-Phe-Phe-Phe-D-Trp-Lys-Thr-Phe-Thr-NH$_2$.

14. An octapeptide of claim 7 of the formula:

D-Phe-Phe-Tyr-D-Trp-Lys-Val-Phe-Thr-NH$_2$.

15. An octapeptide of claim 7 of the formula:

D-Phe-p-Cl-Phe-Tyr-D-Trp-Lys-Val-Phe-Thr-NH$_2$.

16. An octapeptide of claim 7 of the formula:

D-Phe-Ala-Tyr-D-Trp-Lys-Val-Ala-β-D-Nal-NH$_2$.

* * * * *